United States Patent [19]

Chmelir et al.

[11] Patent Number: 5,340,853
[45] Date of Patent: Aug. 23, 1994

[54] POLYMER-BASED SWELLING AND ABSORBING AGENTS WITH AN IMPROVED DEGRADABILITY AND AN IMPROVED ABSORPTION FOR WATER, AQUEOUS SOLUTIONS AND BODY LIQUIDS AND THE USE OF SAID AGENTS FOR THE PRODUCTION OF HYGIENIC ARTICLES AND FOR SOIL CONDITIONING

[75] Inventors: Miroslav Chmelir; Helmut Klimmek, both of Krefeld, Fed. Rep. of Germany

[73] Assignee: Chemische Fabrik Stockhausen GmbH, Krefeld, Fed. Rep. of Germany

[21] Appl. No.: 761,075

[22] Filed: Sep. 17, 1991

[30] Foreign Application Priority Data

Sep. 19, 1990 [DE] Fed. Rep. of Germany ....... 4029592

[51] Int. Cl.$^5$ .......................... C08K 5/15; C08G 63/48; C08G 63/91; C08L 5/00
[52] U.S. Cl. .......................... 524/56; 524/54; 524/55; 525/54.23; 525/54.31; 525/54.32; 604/368; 604/372
[58] Field of Search ................. 524/54, 55, 56, 35–36, 524/41, 43, 45, 47, 48, 50; 525/54.31, 54.32, 54.23; 604/372, 368

[56] References Cited

U.S. PATENT DOCUMENTS

| | | | |
|---|---|---|---|
| 3,658,734 | 4/1972 | Pettitt | 524/55 |
| 3,740,360 | 6/1973 | Nimerick | 524/55 |
| 4,076,663 | 2/1978 | Masuda et al. | 525/54.31 |
| 4,143,007 | 3/1979 | DeMartino | 524/55 |

FOREIGN PATENT DOCUMENTS

| | | |
|---|---|---|
| 2650377 | 5/1977 | Fed. Rep. of Germany. |
| 0189169 | 10/1984 | Japan ................. 524/56 |

OTHER PUBLICATIONS

DATABASE WPIL, Accession No. 81-55765D [31], Derwent Publications Ltd., London, GB; & JP-A-56 070 011 (Lion Corp.).

Primary Examiner—Paul R. Michl
Assistant Examiner—LaVonda DeWitt

[57] ABSTRACT

The present invention relates to an absorbing and swelling agent for water, aqueous solutions and body liquids, which consists of a mixture of at least two components, whereby component A is at least a water-swellable, synthetic polymer or copolymer cross-linked with a polyfunctional compound, and component B is at least a polysaccharide selected from the group consisting of galactomannans or polygalactomannans, as well as galactomannan derivatives or mixtures thereof with other natural or synthetic polymers which at normal temperature are present as pourable powders or as fibrous materials and are only partially soluble or insoluble in water. The invention further relates to the use of said absorber for the production of hygienic articles, for medical purposes, and for soil conditioning,

10 Claims, No Drawings

POLYMER-BASED SWELLING AND ABSORBING AGENTS WITH AN IMPROVED DEGRADABILITY AND AN IMPROVED ABSORPTION FOR WATER, AQUEOUS SOLUTIONS AND BODY LIQUIDS AND THE USE OF SAID AGENTS FOR THE PRODUCTION OF HYGIENIC ARTICLES AND FOR SOIL CONDITIONING

The present invention relates to polymers consisting of a combination of synthetic polymers and natural polymers belonging to the group of galactomannans, said polymers rapidly absorb water, aqueous liquids, and body liquids. The present invention further relates to the use of said polymers for the production of hygienic articles (e.g., disposable products, such as diapers, sanitary towels, and incontinence articles) and water-storing soil conditioners.

Absorbents having a high absorption capacity for water and body liquids are known. Those belonging to the fully synthetic absorbing agents are cross-linked polymers and copolymers on the basis of acrylic or methacrylic acid (German OS [Offenlegungsschrift, publication of a German patent application] Nos. 24 29 236, 26 14 662, 27 12 043, 26 53 135, 26 50 377, 28 13 634; U.S. Pat. Nos. 4,018,951, 3,926,891, 4,066,583, 4,062,817), maleic acid derivatives (according to U.S. Pat. No. 4,041,228), or acrylamidopropane sulfonic acid copolymers (according to German Pat. No. 31 24 008). These known synthetic absorbing agents are practically insoluble in water, absorb the multiple of their weight of water, urine, or other aqueous solutions at equilibrium, however, they are relatively resistant to biodegradability.

Other products were produced on starch basis, e.g., starch acrylonitrile graft polymers (according to U.S. Pat. Nos. 3,997,484, 3,661,815, 4,155,888 and 3,935,099), gelatinized starch derivatives (according to German OS 27 02 781), or on a cellulose basis, such as derivatives of alkyl- or hydroxyalkyl cellulose (JP-Pat. No. 77/125 481), carboxymethylcellulose (according to BE-Pat. No. 862 130 and GB-Pat. No. 1 159 949) and on a polysaccharide basis (German OS 26 50 377). Although these products, such as the starch polymers grafted with acrylonitrile or acrylic acid, belong to the degradable products, their production is very expensive and the amount of the natural product in the final product is very limited due to the high viscosity of the reaction medium, e.g., in case of a monomer solution with dissolved starch.

Although the natural swelling agents based on polysaccharide are used in the foodstuff industry and in medicine in large quantities, they are of minor importance for the use as absorbents for water and aqueous solutions since they exhibit only low absorption capacities. According to British Pat. No. 2 144 759, a composition consisting of pectin (15 to 60%) and 15 to 80% cellulose-containing material absorbs only two to five times the amount as compared to a conventional cellulose material. However, the biodegradability of such natural swelling agents is of advantage since the natural macromolecules, such as cellulose, starch, proteins, etc., in biological systems are decomposed by hydrolysis and subsequent oxidation within a relatively short period of time.

According to U.S. Pat. No. 4,624,868, the absorption capacity of guar gum can considerably be improved by cross-linking it with borax, however, highly diluted solutions (1 to 2%-wt. guar flour in water) have to be used so that the subsequently required evaporation of large water amounts render such a procedure inefficient.

Guar gum cross-linked with borate anion and used as absorber in a diaper construction with an absorption capacity of 10 ml/g (water) is described by U.S. Pat. No. 3,903,889, and one having an absorption capacity of 20 ml/g is described by U.S. Pat. No. 3,070,095. A physical mixture of a linear or branched, water-soluble polyacrylic acid salt (molecular mass 10,000 to $10.10^6$) or a partially hydrolysed graft copolymer of starch and acrylamide with guaran gum, xanthan gum, or alginates also results in an improved absorption capacity for synthetic urine or horse blood, respectively, used as test liquids (German OS 26 50 377). In these cases, however, both components are water-soluble and thus unsuitable, e.g., in a modern diaper construction, due to the extremely large quantities of water-extractable components.

A further use of guar gum as thickening agent of the monomer solution in the polymerization initiated by ionizing irradiation is described by German OS 27 37 994. In this case, starch, xanthan, guar, or other thickeners are added to the monomer solution prior to polymerization to solidify an evenly thick layer of the monomer solution from the upper edge to the bottom of a U-shaped radiation vessel and thus prevent the thickened monomer solution from flowing down the vertical walls of the vessel. An even distribution of the monomer solution in thin layer and an equal distance around the radiation source is absolutely necessary to achieve good effectivity of the high-energy irradiation. Compared to products which are cross-linked by high-energy irradiation (C-C-cross-linkage), products cross-linked with polyfunctional compounds are said to be less suitable for the use as absorbers for aqueous liquids.

Guar gum combined with carrageen, agar, or xanthan used as thickener in foodstuffs is described by German OS 33 35 593, and used as thickener in the production of fertilizers by British Pat. No. 1 437 266.

The medical application of guar gum is based on the fact that it is not hydrolyzed enzymatically and thus not absorbed after oral administration; it delays the absorption of nutrients, acts like an appetite depressant, reduces the cholesterol content in the blood, and regulates the peristalsis. Since, however, swelling takes place very rapidly in case of commercial guar gum, whereby a mucid, highly viscous and adhesive mass results, there is an extreme danger of suffocation, when guar gum is taken orally in dry condition, since the swollen guar gum may seal up the mouth, throat, and gullet. The intake in liquid condition requires large amounts of liquid to be taken in addition (400 ml per 4 g of guar gum) due to the high viscosity of the solutions. According to European OS 0 241 710, swelling takes place slowlier, if coarse-ground guar gum (grain size 50 to 1500 μm) is used.

It is accordingly the object of the present invention to provide absorbing agents exhibiting the advantages of a high absorption capacity for water and body liquids inherent, in the synthetic absorbers but without the resistance to biodegradability thereof.

According to the present invention this object is achieved by a mixture consisting of at least two components A and B, whereby component A is at least a water-swellable, synthetic polymer or copolymer cross-linked with a polyfunctional compound, and component B is at least a polysaccharide selected from the group consisting of the galactomannans or polygalactomannans, as well as the galactomannan derivatives or mixtures thereof with other natural or synthetic polymers which are present at normal temperature as pourable powders or as fibrous materials and are partially soluble or insoluble in water.

Surprisingly, it was found that when a polysaccharide belonging to the group of galactomannans, e.g., guar gum which substantially consists of galactomannans and on its own only has a moderate swelling capability for synthetic model urine (5 to 6 ml/g), is added to another synthetic, cross-linked polymer (component A), the absorption capacity of said mixture consisting of components A and B is considerably increased.

The mixing ratio of the two components A and B may vary within wide ranges. For example, the absorption and swelling agent according to the present invention may contain 20 to 98%-wt., preferably 50 to 90%-wt., of component A, and 2 to 80%-wt., preferably 10 to 50%-wt., of component B.

The production of the end product composed of components A and B may be effected in the most simple case by simply mixing the two components in dry (powdery), moist or slightly swollen condition of either one or both components.

According to another embodiment of the present invention, component B may also be added to the synthetic polymer A in the form of a powder or in slightly swollen form during the production process of component A. In this case, the end product is an absorption and swelling agent in which component B is incorporated in the synthetic polymer of component A by a chemical reaction and/or physical interaction. Compared to a physical mixture of the two components, this procedure reduces the water-extractable components in the end product. In this embodiment, it is preferred to add component B to the swollen polymer gel of component A in dry condition as a powder, or in slightly moist to swollen condition only during the end phase of component A's production process, i.e., not before a polymer conversion of more than 60%, preferably more than 90% is achieved, and to process it further afterwards. Generally, component B will be added up to a polymer conversion of 95%, but it may also be added in case of higher polymerization reaction rates of up to 99%.

The production of component A as swollen polymer gel may be effected discontinuously in a polymerization vessel or continuously on a continuous belt. According to German Pat. No. 35 44 770, e.g., the polymerization is carried out in an aqueous solution containing the water-soluble monomer and, optionally, the comonomers at a concentration of 2.2 to 8.3 mols of polymerizable double bonds per kilogram of monomer solution, in particular 3.5 to 6.25 mols (corresponding to 16 to 60%-wt., particularly 25 to 45%-wt. acrylic acid, if it is used as monomer) and within a temperature range of approximately $-10°$ C. to $120°$ C.

The polymers of acrylic acid and methacrylic acid alone as homopolymer or as copolymer are primarily suitable for the use as component A, but the polymers of other water-soluble monomers are also suitable, such as (meth-)acrylamide and (meth-)acrylonitrile, vinyl pyridine, vinyl pyrrolidone, vinyl acetate, as well as other water-soluble monomers, such as polymerizable acids and the salts thereof, in particular maleic acid, fumaric acid, itaconic acid, vinyl sulfonic acid, or 2-acrylamido-2-methylpropane sulfonic acid. Further examples are hydroxyl-groups-containing esters of polymerizable acids, in particular the hydroxyethyl and hydroxypropyl esters of acrylic and methacrylic acid; as well as amino-groups-containing and ammonium-groups-containing esters and amides of polymerizable acids, such as the dialkylamino esters, in particular the dimethyl- and the diethylaminoalkyl esters of acrylic and methacrylic acid, as well as the trimethyl- and triethylammonium alkylesters and the corresponding amides thereof.

Small amounts of the cross-linking monomers, e.g., monomers having more than one polymerizable group within the molecule, are polymerized together with the above-mentioned monomers, whereby cross-linked homo- or cross-linked copolymers result.

If the described monomers are polymerized alone only with the addition of a cross-linking agent (in small amounts, as compared to the monomer concentration), cross-linked homopolymers result. When a mixture of several monomers and a small amount of cross-linking agent are polymerized, the resulting products are defined as cross-linked copolymers.

Small amounts of water-insoluble monomers may be co-polymerized, such as the esters of acrylic and/or methacrylic acid with $C_1-C_{10}$-alcohols, styrene and alkylated styrenes. In general, the proportion of water-soluble monomers is in the range of 40 to 100%-wt., relative to the total amount of monomers. The proportion of the cross-linking comonomers is in the range of 0.01 to 20%-wt., preferably 0.01 to 2.0%-wt., relative to the total monomer amount. In general, the quantity of water-insoluble (hydrophobic) monomers amounts to 0 to 40%-wt. of the monomers.

Examples of cross-linking monomers include bi- or polyfunctional monomers, e.g., amides, such as the methylene bisacryl- or -methacrylamide or ethylene bisacrylamide, in addition esters of the unsaturated mono- and multivalent carboxylic acids of polyols, such as diacrylates or triacrylates, e.g., butanediol- or ethylene glycol diacrylate or -methacrylate, trimethylolpropane triacrylate, as well as vinyl methacrylate and allyl compounds, such as allyl(meth) acrylate, triallyl cyanurate, maleic acid diallyl ester, polyallyl ester, tetraallyl oxiethane, triallylamine, tetraallyl ethylene diamine, allyl ester of the phosphoric acid or phosphorous acid, respectively, as well as cross-linkable monomers, such as the N-methylol compounds of amides, such as methacrylamide or acrylamide and the ethers derived therefrom.

The polymerization may be initiated by chemical catalysis and/or high-energy radiation/light. Suitable catalysts, for example, are peroxy compounds, such as potassium peroxydisulfate, hydrogen peroxide, organic peroxides, such as benzoyl peroxide, tert-butyl hydroperoxide, tert-butyl perpivalate; redox systems, such as potassium-peroxydisulfate-sodium-disulfite, hydrogen peroxide hydroxylamine chloride, or azoinitiators, such as AIBN [2,2'-azobis-(isobutyronitrile)] or 2,2'-azobis(2-amidinopropane)dihydrochloride. Examples of suitable photoinitiators include benzoin and the derivatives thereof, e.g., benzoin ether, such as benzoin-ethyl-propyl-ether, benzil and the derivatives thereof, such as benzil ketals or aryl diazonium salts, acetophenone derivatives, and others, alone or in admixtures and/or even in mixtures with peroxide-containing catalyst systems or azoinitiators. In general, the content of photoinitiators is in the range of 0.002 to 2.0%-wt., preferably 0.0to 0.2%-wt., relative to the monomers used. The catalyst content generally is in the range of 0.02 to 5.0%-wt., preferably between 0.20 to 2.0%-wt., relative to the monomers.

As component B the polysaccharides belonging to the group of galactomannans, which are contained, e.g., in guar gum or locust bean gum, are used alone or in admixtures with other natural polymers based on polysaccharide, such as cellulose and the derivatives thereof (e.g., alkyl-, hydroxyalkyl-, carboxymethylcellulose), viscose fibers, gum resins (e.g., tragacanth gum, gum arabic, pectin, dextran, etc.); starch and starch derivatives (e.g., corn starch, grain starch, potato starch, amylose, amylopectin, dextrin, modified starch, hydroxyethyl starch, cationic starch, starch graft polymers, etc).

In addition to said natural polymers, other large-surface materials may be used for the mixing with component A, examples thereof include fibrous material of natural fibers, preferably fibers of cotton, wool, and silk, as well as fibrous material of cellulose fibers, such as viscose-, acetate- and triacetate fibers, or of synthetic fibers based on polyester, polyolefins, polyacrylonitrile, polyamide, polyvinyl alcohol, polyvinyl acetate, and polyvinyl chloride, polyurethane, polyvinyl urea, as well as the copolymers of these polymers. The fibrous materials may preferably be incorporated into the component A together with the above-mentioned galactomannans in the form of short fibers.

By means of further processing the mixture of the two components in a mixer with a rotary stirring mechanism and subsequent drying of the polymer gel mass, an end product is obtained in which the guar polymer (component B) is bound in the synthetic polymer, so that—compared to a physical mixture of the two components—the amount of extractables is considerably smaller. Depending on the content of the partially water-soluble component B, end products with soluble portions below 30%-wt., preferably below 20%-wt. are obtained. It is preferred to effect the drying at temperatures in the range of 50° to 160° C.

The incorporation of component B into the synthetic polymer may be intensified in that different already mentioned catalysts in an amount of 0.01 to 2.0%-wt., and/or the above-mentioned polyfunctional monomers in an amount of 0.05 to 5.0%-wt. are added to component B or component A. The catalysts or polyfunctional compounds may, for example, be sprayed as a solution on component A or B either prior or during mixing thereof.

Mixing the two components may be carried out in a suitable mixer. The mixer used in the present specification consisted of a vertically or horizontally positioned metal cylinder; the stirrer thereof was provided with guide blades thoroughly wiping the walls of the mixer. Once a certain speed of the stirrer was achieved, the two components were evenly mixed and kneaded over the total length of the metal cylinder.

The final product consists of components A and B at a weight ratio of 20 to 98%-wt., preferably 50 to 90%-wt, of component A, and 2 to 80%-wt., preferably 10 to 50%-wt., of component B.

The end products manufactured of components A and B according to the process of the present invention exhibit a clearly improved absorption capacity for synthetic model urine, whereby their biodegradability has been improved as well. Through mixing the two components A and B a synergistic effect is achieved which primarily results in an increased retention value, i.e., in an increased absorption under load. The absorption under pressure and load belongs to the most important criteria in evaluating the value of a superabsorber.

Test methods

1) To determine the rate of absorption, the absorption of model urine is carried out according to the Demand-Absorbency-Test (DAT-method according to W. F. Schlauch, lecture during Index 1978, Amsterdam); the absorption rate after 60 seconds, as well as the maximum absorption and the retention are determined. The measuring instrument consists of a burette filled with model urine solution (2.0% urea, 0.9% NaCl, 0.1% $MgSO_4$, and 0.06% $CaCl_2$, dissolved in distilled water) and a table provided with an outlet opening for the model urine solution connected to the measuring burette. On the table, which was covered with a non-woven ($10 \times 13.5$ cm), 0.5 g of the product according to the present invention, mixed with 5 mg Aerosil 200 (Degussa AG), is evenly sprinkled on the middle of the liquid outlet in the form of a circular area having a diameter of 4.5 cm. The contact of the model urine solution with the powder product is effected by closing the hose and slight pressure loading; the solution of model urine may now be absorbed by the product according to the present invention. After 20 to 30 minutes, the absorbed amount of model urine solution is read as maximum value. Subsequently, the retention is determined by loading the swollen polymer gel with a weight of 10 $g/cm^2$; loading is effected for 5 minutes. The determined retention values are tabulated in the examples.

2) A tea bag test was carried out as additional method to determine the rate of lliquid absorption. The liquid absorption of 0.2 g test substance without added Aerosil 200 was gravimetrically determined in a tea bag after 10 minutes (maximum value) and after centrifuging, e.g., in a commercial centrifuge at 1400 rpm, this value was then converted to 1 g of product (retention value). The aqueous 0.9% NaCl-solution was used as test liquid.

3) Artificial decomposition conditions effected by irradiation similar to daylight were simulated with a Xenotest lamp and exposure times of 30, 60, and 90 minutes using a polymer gel swollen with water (200 g water per 1 g product). The swollen polymer gel was exposed to the Xenotest lamp light, and after certain intervals of time, the degradability of the polymer gel was assessed according to a scale with 1 to 8 grades (Example 21).

Grade 1: gel structure unchanged
Grade 2: gel structure slightly changed
Grade 3: gel structure still detectable, but slight flow
Grade 4: gel structure extremely flown
Grade 5: gel structure not detectable, a highly viscous liquid
Grade 6: low-viscous liquid
Grade 7: liquid ressembling water
Grade 8: water completely evaporated The Xenotest lamp corresponds in the spectral region to natural daylight; the method was developed by Cassella Farbwerke, Mainkur AG, Frankfurt, FRG.

The invention is more particularly described in the following examples which are intended to illustrate, but not to limit, the present invention.

EXAMPLES 1 TO 9

An acrylic acid polymer which was cross-linked with 0.7%-wt. methylene bisacrylamide and present to approximately 70% as sodium salt at a particle size fraction of 100 to 650 μm (component A) was mixed in different proportions with component B, a finely ground Guaran Polymer KWL 2000 (Roeper, Hamburg); the absorption capacity of the mixture was determined according to the DAT-method with synthetic model urine. The results are listed in Table 1 wherein the values for the individual components are listed as comparison examples as well.

Through mixing the two components A and B, a synergistic effect is achieved which primarily results in an increased retention value, i.e., in an increased absorption under load. The absorption under pressure and load belongs to the most important criteria in evaluating a superabsorber.

Table 1 reveals that the retention value of the mixture only slightly changes within a concentration range of up to 33%-wt. with increasing addition of the guar polymer, which itself only has a relatively low retention value (4.8 ml/g), to component A; it even is slightly higher than that of component A alone. Converted to the content of component A in the mixture, leaving alone or considering the absorption values of the guar polymer (Ret$^{(b)}$ and Ret$^{(c)}$), a clear improvement of the retention values of the mixture can be recognized.

Notes (relating to Tables 1 and 2)

The DAT-values Max$^{(a)}$ and Ret$^{(a)}$ relate to 1 g of the product composed of components A and B;

The DAT-values Max$^{(b)}$ and Ret$^{(b)}$ relate to 1 g of component A in the product, whereby the influence of component B on the absorption values has been neglected;

The DAT-values Max$^{(c)}$ and Ret$^{(c)}$ relate to 1 g of component A in the product, whereby the influence of component B on the absorption values has been taken into account in the calculation.

TABLE 1

| | Composition of product | | |
|---|---|---|---|
| | Component A (%-wt.) | Component B (%-wt.) | Weight (g) |
| | 100 | — | 0.5 |
| | — | 100 | 0.5 |
| Ex. 1: | 98 | 2 | 0.51 |
| Ex. 2: | 95 | 5 | 0.52 |
| Ex. 3: | 91 | 9 | 0.55 |
| Ex. 4: | 83 | 17 | 0.60 |
| Ex. 5: | 67 | 33 | 0.75 |
| Ex. 6: | 60 | 50 | 1.00 |
| Ex. 7: | 45 | 55 | 0.50 |
| Ex. 8: | 40 | 60 | 0.50 |
| Ex. 9: | 33 | 67 | 0.50 |

| | Determination of the DAT-values | | | | | |
|---|---|---|---|---|---|---|
| | Max$^{(a)}$ (ml/g) | Ret$^{(a)}$ (ml/g) | Max$^{(b)}$ (ml/g) | Ret$^{(b)}$ (ml/g) | Max$^{(c)}$ (ml/g) | Ret$^{(c)}$ (ml/g) |
| | 50.3 | 26.9 | 50.3 | 26.9 | 50.3 | 26.9 |
| | 6.1 | 4.8 | — | — | — | — |
| Ex. 1: | 49.2 | 26.8 | 50.2 | 27.3 | 50.1 | 27.2 |
| Ex. 2: | 48.1 | 27.2 | 50.5 | 28.6 | 50.2 | 28.4 |
| Ex. 3: | 45.6 | 27.9 | 50.2 | 30.7 | 49.7 | 30.3 |
| Ex. 4: | 40.5 | 29.8 | 48.6 | 35.8 | 47.6 | 35.0 |
| Ex. 5: | 32.7 | 29.5 | 49.0 | 44.3 | 47.0 | 42.7 |
| Ex. 6: | 18.9 | 18.4 | 37.8 | 36.7 | 34.8 | 34.3 |
| Ex. 7: | 19.1 | 17.1 | — | — | 35.0 | 32.1 |
| Ex. 8: | 16.8 | 15.5 | — | — | 32.8 | 31.6 |
| Ex. 9: | 13.2 | 11.8 | — | — | 27.0 | 26.0 |

EXAMPLES 10 TO 13

50 g of the cross-linked polyacrylate of Examples 1 to 9 were suspended in the same weight amount of a water/methanol mixture (25:75) and thereby preswollen. Component B (Guaran-Polymer KWL 2000) was then added to this suspension; stirring for 15 minutes. Subsequently, the suspension was filtered by suction and dried at 50° C. under vacuum. The determined results are summarized in Table 2.

TABLE 2

| | Composition of product | | |
|---|---|---|---|
| | Component A (%-wt.) | Component B (%-wt.) | Weight (g) |
| | 100 | — | 0.5 |
| | — | 100 | 0.5 |
| Ex. 10: | 91 | 9 | 0.55 |
| Ex. 11: | 83 | 17 | 0.60 |
| Ex. 12: | 83 | 17* | 0.60 |
| Ex. 13: | 67 | 33 | 0.75 |

| | Determination of the DAT-values | | | | | |
|---|---|---|---|---|---|---|
| | Max$^{(a)}$ (ml/g) | Ret$^{(a)}$ (ml/g) | Max$^{(b)}$ (ml/g) | Ret$^{(b)}$ (ml/g) | Max$^{(c)}$ (ml/g) | Ret$^{(c)}$ (ml/g) |
| | 49.8 | 26.5 | 49.8 | 26.5 | 49.8 | 26.5 |
| | 5.5 | 2.2 | — | — | — | — |
| Ex. 10: | 46.7 | 27.1 | 51.4 | 29.8 | 51.0 | 29.6 |
| Ex. 11: | 42.9 | 29.0 | 51.5 | 34.8 | 50.6 | 34.4 |
| Ex. 12: | 41.6 | 29.7 | 49.9 | 35.6 | 49.0 | 35.2 |
| Ex. 13: | 33.9 | 30.1 | 50.9 | 45.2 | 43.4 | 44.5 |

Note:
*)pre-swollen with water-methanol-mixture 50:50

EXAMPLE 14

The component A (1 g) of Examples 1 to 13 was mixed with 0.25 g of a mixture of component B (guaran-polymer/carboxymethylcellulose 50:50); the absorption capacity was determined according to the DAT-method. The end product exhibited a maximum value of 58.2 ml and a retention value of 45.8 ml. For comparison purposes: Component A has a maximum value of 50.2 ml/g and a retention of 26.5 ml/g.

EXAMPLES 15 TO 17

In a polymerization vessel, 410 g acrylic acid and 2.6 g triallylamine (0.6%-wt., relative to acrylic acid) were dissolved in 670 ml water and partially neutralized with 376 g caustic soda lye (45%). The catalyst components 0.15 g benzil dimethyl ketal (Irgacure 651, Ciba-Geigy) and 1.5 g sodium peroxidisulfate, dissolved in 25 ml water, were added at room temperature and the adiabatic polymerization was started. The resulting polymer gel was cut into pieces, evenly sprayed with 2000 ppm (relative to dry substance in polymer gel) sodium peroxidisulfate, dissolved in 30 ml water, and then processed for 30 minutes with different amounts of Guaran-Polymer in a mixer, the stirring mechanism of which was provided with guide blades thoroughly wiping the walls of the mixing cylinder. The resulting mass of polymer gel was then dried at 120° C. The absorption capacity of the final product was determined according to the tea bag test (Table 3).

TABLE 3

| | Composition of product | | Tea bag test values | | |
|---|---|---|---|---|---|
| | Component A acrylic acid polymer %-wt. | Component B guaran polymer %-wt. | maximum (ml/g) | retention (a) (ml/g) | (b) (ml/g) |
| | 100 | 0 | 41.0 | 27.1 | 27.1 |
| | 0 | 100 | 6.0 | 2.5 | — |
| Example 15: | 80 | 20 | 37.9 | 27.3 | 34.1 |
| Example 16: | 60 | 40 | 38.2 | 23.5 | 39.2 |

TABLE 3-continued

| Composition of product | | Tea bag test values | | |
|---|---|---|---|---|
| Component A acrylic acid polymer %-wt. | Component B guaran polymer %-wt. | maximum (ml/g) | retention (a) (ml/g) | (b) (ml/g) |
| Example 17: 50 | 50 | 38.1 | 22.7 | 45.4 |

Note:
The tea bag test values maximum and retention (a) relate to 1 g of the product composed of components A and B, retention (b) relates to 1 g of Component A within the product.

EXAMPLES 18 TO 20

237 g acrylic acid, 357 g acrylamide and 2.3 g N,N'-methylene bisacrylamide were dissolved in 975 ml water in a polymerization vessel and neutralized with 371 g potash lye (45%). The catalyst components (0.26 g azobisamidine propane dihydrochloride, 0.06 g Irgacure 651, and 0.26 g t-butyl hydroperoxide, dissolved in water) were added at room temperature and the adiabatic polymerization started with UV-light. The achieved conversion of reaction was 99.5%. The copolymer gel was cut into pieces and was mixed with different ratios of guaran polymer and polyamide short fibers (1.0 mm, 6.7 dtex) in a mixing apparatus as in Examples 15 to 17; the resulting product was then dried. In addition, the absorption rate was determined as teabag test-value after 15 minutes of dipping (Table 4). The incorporation of the polyamide fibers together with the guaran polymer into the cross-linked copolymer resulted in a quicker absorption of the test liquid.

TABLE 4

| | Component A acrylic acid/ acrylamide copolymer (%-wt.) | Component B | | tea bag test-values | | | | |
|---|---|---|---|---|---|---|---|---|
| | | guaran polymer (%-wt.) | polyamide fibers (%-wt.) | max. (a) (ml/g) | (b) (ml/g) | ret. (a) (ml/g) | (b) (ml/g) | 15-sec. value |
| | 100 | 0 | 0 | 39.5 | 39.5 | 27.3 | 27.3 | 11.0 |
| Ex. 18: | 80 | 20 | 0 | 35.8 | 44.7 | 24.3 | 30.4 | 10.9 |
| Ex. 19: | 80 | 10 | 10 | 36.6 | 45.7 | 22.0 | 27.5 | 14.2 |
| Ex. 20: | 70 | 20 | 10 | 34.3 | 49.0 | 19.6 | 28.0 | 16.4 |

Note:
The tea bag test values maximum (a) and retention (a) relate to 1 g of the product composed of components A and B, maximum (b) and retention (b) relate to 1 g of component A in the product.

EXAMPLE 20

The powdery product of Examples 15 to 17 was swollen in water (200 g water per 1 g product) and, as swollen gel, subsequently irradiated with the Xenotest lamp to simulate degradation conditions under daylight. After 30, 60, and 90 minutes, the degradability of the polymer gel was assessed according to a scale with grades 1 to 8. The results are listed in Table 5 which shows the improved degradability of the composed products.

TABLE 5

| | Component A Acrylic acid polymer %-wt. | Component B Guaran polymer %-wt. | Exposure times Minutes | | |
|---|---|---|---|---|---|
| | | | 30 | 60 | 90 |
| | 100 | 0 | 2 | 4 | 5 |
| Ex. 15: | 80 | 20 | 5 | 6 | 6 |
| Ex. 16: | 60 | 40 | 5 | 6 | 7 |
| Ex. 17: | 50 | 50 | 6 | 6 | 7 |

Grade 1: gel structure unchanged
Grade 2: gel structure slightly changed
Grade 3: gel structure still detectable, but slight flow
Grade 4: gel structure extremely flown
Grade 5: gel structure not detectable, a highly viscous liquid
Grade 6: low viscous liquid
Grade 7: liquid ressembling water
Grade 8: water completely evaporated It is understood that the specification and examples are illustrative but not limitative of the present invention and that other embodiments within the spirit and scope of the invention will suggest themselves to those skilled in the art.

What is claimed is:

1. An absorbing and swelling agent for water, aqueous solutions and body liquids consisting of a physical mixture of at least two components, wherein component A is a water-swellable, synthetic polymer or copolymer crosslinked with a multifunctional compound, and component B is a polysaccharide selected from the group consisting of (i) the galactomannans, (ii) the polygalactomannans, and (iii) admixtures of a galactomannan or polygalactomannan with other natural or synthetic polymers selected from the group consisting of cellulose, alkyl cellulose, hydroxyalkyl cellulose, carboxymethyl cellulose, viscose, tragacanth gum, gum arabic, pectin, dextran, starch, amylose, amylopectin, dextrin, modified starch, hydroxyethyl starch, cationic starch, a starch graft polymer, cotton, wool, silk, cellulose acetate, cellulose triacetate, polyester, polyolefin, polyacrylonitrile, polyamide, polyvinyl alcohol, polyvinyl acetate, polyvinyl chloride, polyurethane, polyvinyl urea and copolymers thereof, which mixture of A and B is present as a pourable powder or fibrous material and is partially soluble or insoluble in water.

2. An absorbing and swelling agent according to claim 1, produced by adding component B in dry or slightly humid or swollen condition during the production of component A after a polymer conversion of more than 60% is attained, and by subsequent drying.

3. An absorbing and swelling agent according to claim 1, wherein component A is a cross-linked homopolymer or copolymer of acrylic acid, methacrylic acid, acrylamidopropane sulfonic acid, of an alkali metal or ammonium salt of these carboxylic acids, of acrylamide or methacrylamide or a derivative thereof, of vinyl pyrrolidone, or a copolymer of any of the above with a monomer which is only partially water-soluble.

4. An absorbing and swelling agent according to claim 1, wherein component B is (i) guar gum, (ii) locust bean gum or (iii) a mixture of guar gum or locust bean gum with an additional polysaccharide or derivative thereof selected from the group consisting of starch, dextrin, dextran, cellulose and derivatives thereof.

5. An absorbing and swelling agent according to claim 1, wherein component B is guar gum or locust bean gum in admixture with natural or synthetic fibers.

6. An absorbing and swelling agent according to claim 2, wherein component B is incorporated within the synthetic polymer component A so that the water-extractable content of the end product is smaller than 30%-wt. relative to component B.

7. An absorbing and swelling agent according to claim 1, comprising 20 to 98%-wt. of component A and 2 to 80%-wt. of component B.

8. An absorbent disposable product for hygienic, surgical or medical purposes containing an absorbent according to claim 1.

9. An orally administrable swelling agent, an additive for contrast media, an agent for the regulation of the peristalsis, or an oral administrable agent to delay the absorption or action of taken drugs, or to lower the cholesterol level containing an absorbent according to claim 1.

10. An absorbent for the subsequent controlled, retarded release of an absorbed liquid and a substance optionally dissolved therein to biological systems, seeds, plants, or microorganisms to function as a nutrient or preventive containing an absorbent according to claim 1.

* * * * *